(12) United States Patent
Xu et al.

(10) Patent No.: US 12,383,649 B2
(45) Date of Patent: Aug. 12, 2025

(54) SAFE DISPOSAL MACHINE FOR PERITONEAL DIALYSIS LIQUID WASTE

(71) Applicant: Ningbo No. 2 Hospital, Zhejiang (CN)

(72) Inventors: Lingcang Xu, Zhejiang (CN); Haixue Lin, Zhejiang (CN); Fangfang Zhou, Zhejiang (CN); Qun Luo, Zhejiang (CN); Beixia Zhu, Zhejiang (CN); Congping Xue, Zhejiang (CN); Meng Li, Zhejiang (CN); Zhiwei Dai, Zhejiang (CN); Qilin Sheng, Zhejiang (CN)

( * ) Notice: Subject to any disclaimer, the term of this patent is extended or adjusted under 35 U.S.C. 154(b) by 379 days.

(21) Appl. No.: 18/123,938

(22) Filed: Mar. 20, 2023

(65) Prior Publication Data
US 2023/0302184 A1    Sep. 28, 2023

(30) Foreign Application Priority Data
Mar. 28, 2022    (CN) .......................... 202210310687.3

(51) Int. Cl.
*A61L 2/26*    (2006.01)
*A61L 2/10*    (2006.01)
*A61L 2/18*    (2006.01)
*A61L 2/24*    (2006.01)

(52) U.S. Cl.
CPC .................... *A61L 2/26* (2013.01); *A61L 2/10* (2013.01); *A61L 2/18* (2013.01); *A61L 2/24* (2013.01); *A61L 2202/122* (2013.01); *A61L 2202/17* (2013.01)

(58) Field of Classification Search
CPC ..... A61L 2/10; A61L 2/18; A61L 2/22; A61L 2/24; A61L 2/26; A61L 2202/122; A61L 2202/14; A61L 2202/17; A61L 2202/23; Y02W 30/10
See application file for complete search history.

(56) References Cited

U.S. PATENT DOCUMENTS

2004/0069718 A1* 4/2004 Sun ..................... B01F 23/2132
                                                    210/748.11

* cited by examiner

*Primary Examiner* — Dirk R Bass

(57) ABSTRACT

A safe disposal machine for peritoneal dialysis liquid waste comprises a box main body, with ultraviolet lamps for box internal disinfection provided at the top of the box's interior, a weighing device for peritoneal dialysis liquid waste weighing provided at the top of a filter plate, a placing and cutting device for drainage bag cutting provided at the top of the weighing device, and a flushing and disinfection device for drainage bag disinfection provided in the box. The invention can weigh the drainage bag, facilitating the recording of the peritoneal dialysis ultrafiltration volume for patients; the placing and cutting device can take down the weighed drainage bag, and simultaneously cut the drainage bag into a cross shape to pull outwards; the drainage bag capable of inner-side turning over can facilitate the complete washing through flushing and disinfection device, to avoid the residual liquid waste endangering others and the environment.

8 Claims, 13 Drawing Sheets

SAFE DISPOSAL MACHINE FOR PERITONEAL DIALYSIS LIQUID WASTE

1. TECHNICAL FIELD

The invention relates to the field of medical technology, in particular to the safe disposal machine for peritoneal dialysis liquid waste.

2. BACKGROUND ART

Peritoneal Dialysis (PD) utilizes the property of the peritoneum as a semi-permeable membrane to instill the prepared dialysis solution into the peritoneal cavity of the patient through the peritoneal dialysis catheter regularly and periodically by gravity. As there is a solute concentration gradient difference between the two sides of the peritoneum, the solute on the high-concentration side moves to the low-concentration side (diffusion) and the water moves from the hypotonic side to the hyperosmotic side (osmosis). The peritoneal dialysis fluid is constantly replaced to achieve the removal of metabolites and toxic substances from the body and to correct the disturbance of water and electrolyte balance.

Peritoneal dialysis liquid waste is medical waste with some infectious properties. When disposing of the liquid waste, patients may discard it directly along with the waste bag, or they may cut peritoneal dialysis waste bags and pour the liquid waste into the toilet. The cutting process can easily injure the operator, the pouring process can easily spread disease by splashing the infectious liquid waste, and the disposal process of the cut waste bag can also cause disease transmission. All the above operations do not meet the medical waste disposal specifications. Therefore, we propose a safe disposal machine for peritoneal dialysis liquid waste.

3. SUMMARY OF THE APPLICATION

The purpose of the invention is to provide a safe disposal machine for peritoneal dialysis liquid waste to solve the problems in the above background technology.

To achieve the above purpose, the invention provides the following technical solutions: a safe disposal machine for peritoneal dialysis liquid waste comprises a box main body, wherein: the box main body is provided with a liquid waste collection chamber at the bottom, and the liquid waste collection chamber is connected with a drainage pipe at the bottom for drainage of the liquid waste, and the drainage pipe is provided with a one-way valve.

The interior of box main body is provided with ultraviolet lamps for disinfection of the interior of the box main body.

The box main body is provided with a fan on one side, and the box main body is connected with ventilation ducts for venting away from the fan.

The liquid waste collection chamber is provided with a filter plate on top, the filter plate is provided with a weighing device on top for weighing the peritoneal dialysis liquid waste, and the weighing device is provided with a placing and cutting device on top for cutting the drainage bag.

The box main body is provided with a flushing and disinfection device inside for disinfection of the drainage bags.

The box main body is provided with a waste bag outlet on the outside, and an isolation door is slidingly connected inside the waste bag outlet; the isolation door is connected with an electric telescopic rod I on the top, and the electric telescopic rod I is connected with the inside of the waste bag outlet.

The box main body is provided with a transmission belt near the liquid waste bag outlet, and the bottom of the transmission belt is connected with an electric telescopic rod II; the electric telescopic rod II is provided at one end on the outside of the box main body, the transmission belt is provided with an automatic waste bin at one end, and one end of the transmission belt is slidingly connected to the entrance of the automatic waste bin; the transmission belt is provided with infrared detectors on both sides near the box main body, and the infrared detectors are connected to the outer side of the box main body; the transmission belt is provided with a transparent glass cover on the outer side, and the two ends of the transparent glass cover are connected to the box main body (1) and the automatic waste bin respectively.

Preferably, the weighing device comprises a weigher provided at the bottom of the box main body, and the weigher is provided with a fixed mechanism at the top for fixing the drainage bag and drainage pipe.

The weigher is provided with a rotating rod I on the outside, and the rotating rod I is rotatingly connected to L-shaped plates on both sides; the rotating rod I is connected to drive motor I through L-shaped plates at one end, and drive motor I is fixed to the outside of L-shaped plates through a waterproof cover.

The box main body is provided with supporting casings I on both sides inside, the supporting casings I is slidingly connected with supporting block I inside, and the supporting block I is connected to one end of the L-shaped plate on the outside.

The supporting casing I is provided with a drive assembly inside for driving the supporting block I to move.

Preferably, the drive assembly comprises screw rods rotatably connected to the inside of the supporting casings I, and the screw rods are connected to the supporting block I; one end of the screw rods is connected to drive gears through the box main body, and two drive gears are connected in mesh with a gear link; either one of the screw rods is connected to drive motor II through drive gear, and drive motor II is fixed to the outside of the box main body through a waterproof cover.

Preferably, the fixed mechanism comprises a pressure plate I provided at the top ends of the weigher with a clamping hole I, and the pressure plate I is provided with a pressure plate II with a clamping hole II at the top.

The pressure plate II is provided with a rotating rod II on the outside, the rotating rod II is connected to the outside of pressure plate I by rotation at both ends, and one end of the rotating rod II is connected to a drive motor III through pressure plate I, and the drive motor III is fixed to the outside of pressure plate I by a waterproof cover.

Preferably, the placing and cutting device comprises a bottom support plate set and a top support plate set provided at the top of the weigher, allowing the top and bottom of the drainage bag to be fixed respectively; the bottom support plate set and top support plate consist of a plurality of bottom fixed plates and top fixed plates, respectively.

The bottom fixed plates are connected with electromagnets at the top and the top fixed plates are connected with iron sheets corresponding to electromagnets at the bottom; the bottom fixed plates and bottom fixed plates are connected with adsorption mechanisms at the ends close to each other for adsorbing the split portion of the drainage bag.

The bottom fixed plates at the bottom and top fixed plates at the top are connected with connection plates I and connection plates II, respectively; the connection plates I and II are connected on one side with telescopic cylinders I and telescopic cylinders II respectively, and the telescopic cylinders I and II near each other are connected at one end with double-head cylinders; the double-head cylinders on one side are connected to moving plates, and the box main body is provided with moving devices on each side of the interior of the box main body for moving the two moving plates respectively; two moving devices are connected at the top with a U-shaped plate, and the U-shaped plate is connected at the top with a first vertical cylinder, and the first vertical cylinder is connected to the top interior of the box main body.

The moving plates are provided with a clamping assembly on top for clamping the drainage bag and drainage pipe.

The top supporting plate set is provided with a waterjet for cutting the drainage bag at the top, the waterjet is provided with a moving assembly for driving the waterjet to move at the top, and the moving assembly is connected to the bottom of the U-shaped plate.

Preferably, the adsorption mechanism comprises fixed grooves provided on the bottom fixed plates, and micro cylinders I are provided inside the fixed grooves, and the output end of the micro cylinders I is connected to vacuum chucks for adsorption on the cut drainage bags.

Preferably, the mobile devices comprise supporting casings II provided inside the box main body, and the supporting cases II are internally slidingly connected with supporting blocks; the supporting casings II are internally rotationally connected with a threaded rods, and the threaded rod is connected to the supporting block II; the threaded rod through the supporting casings II is connected to the drive motor IV, and the drive motor IV is fixed to the outside of the supporting casings II through the waterproof cover.

Preferably, the clamping assembly comprises a fixed rod I provided at the top of the moving plates, and an output cylinder is provided at the top of the fixed rod I; the output end of the output cylinder is connected to a micro cylinder II, and the output of the micro cylinder II is connected to an L-shaped block; the L-shaped block is connected with two rotating rods III on the inner side, and both the rotating rods III are connected with holding blocks for holding the drainage bag and drainage pipe.

The rotating rod II is provided with connecting gears, and the two connecting gears are connected in mesh; any of the rotating rods III is connected to motor I, and motor I is fixed to the outside of the L-shaped block by a waterproof cover.

Preferably, the moving assembly comprises a fixed casing I provided at the bottom of the U-shaped plate, and the fixed casing I is internally in a rotating connection with a threaded drive rod I; the drive rod I is connected to a rotating motor I through one end of the fixed casing I, and the rotating motor I is fixed to the outside of the fixed casing I by a waterproof cover.

The fixed casing I is internally in the sliding connection with limit block I, and limit block I is connected with drive rod I; the limit block I is connected with fixed casing II at the bottom, and fixed casing II is internally in the rotating connection with threaded drive rod II, and drive rod II is connected with rotating motor II through fixed casing II at one end.

The drive rod II is externally connected to the limit block II, and the limit block II is slidingly connected to the inside of the fixed casing II; the limit block II is connected to the second vertical cylinder at the bottom, and the output end of the second vertical cylinder is connected to the top of the waterjet.

Preferably, the flushing and disinfection device comprises spray pipes provided on both sides of the inside of the box main body, and the spray pipes are connected to the outside of the clear water pipe and disinfection pipe; the box main body is connected with a clear water tank for placing clear water and a disinfection tank for placing disinfection solution on the top, and the clear water pipe and disinfection pipe are connected with the clear water tank and the disinfection tank respectively.

Compared to the prior arts, the invention has the following advantages and beneficial effects:

1. The invention can weigh the drainage bag through the weighing device, facilitating the recording of the peritoneal dialysis ultrafiltration volume for peritoneal dialysis patients; the placing and cutting device can take down the weighed drainage bag, and simultaneously cut the drainage bag into a cross shape and pull the drainage bag outwards; the drainage bag capable of inner-side turning over can facilitate the complete washing of drainage bag through flushing and disinfection device, to avoid the residual liquid waste endangering others and the environment.

2. The device provided by the invention, with the placement of placing and cutting device can move the drainage bag finished with flushing and disinfection to the transmission belt for transmission out, avoiding manual removal of the waste bag and reducing the chance of occupational exposure, which truly achieves fully automatic medical waste classification.

4. BRIEF DESCRIPTION OF ACCOMPANY DRAWINGS

Figure 1:
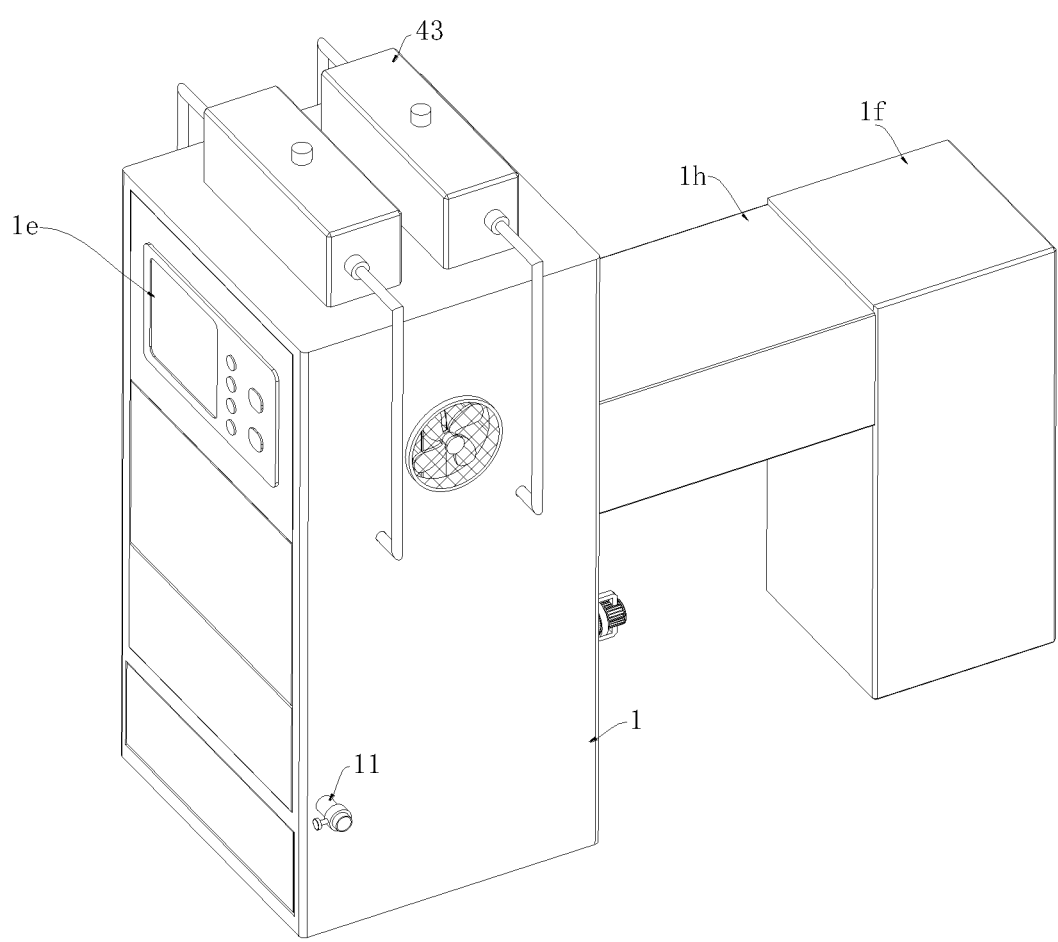
FIG. 1 is a schematic diagram showing the main view structure of the overall structure of the invention.

In the figures, 1. the box main body; 10. the liquid waste collection chamber; 11. the drainage pipe; 12. the one-way valve; 13. the ultraviolet lamps; 14. the fan: 15. the ventilation ducts; 16. the filter plate; 2. the weighing device; 3. the placing and cutting devices; 4. the flushing and disinfection device; 17. the transmission belt; 20. the weigher; 21. the fixed mechanism; 22. the rotating rod I; 23. the L-shaped plates; 24. the drive motor I; 25. the supporting casings I; 26. the supporting blocks I; 5. the drive assembly; 50. the screw rods; 51. the drive gears; 52. the gear link; 53. the drive motor II; 27. the clamping hole I; 28. the pressure plate I; 29. the clamping hole II; 2a. the pressure plate II; 2b. the rotating rod II; 2c. the drive motor II; 30. the bottom supporting plate set; 31. the top supporting plate set; 32. the bottom fixed plates; 33. the top fixed plates; 34. the electromagnets; 35. the iron sheets; 6. the adsorption mechanism; 36. the connection plates I; 37. the connection plates II; 38. the telescopic cylinders I; 39. the telescopic cylinders II; 3a. the double-head cylinders; 3b. the moving plates; 7. the moving devices; 3c. the U-shaped plate; 3d. the first vertical cylinder; 8. the clamping assembly; 3e. the waterjet; 9. the moving assembly; 60. the fixed grooves; 61. the micro cylinders I; 62. the vacuum chucks; 70. the supporting casings II; 71. the supporting blocks II; 72. the threaded rod; 73. the drive motor IV; 80. the fixed rod I; 81. the output cylinder; 87. the micro cylinder II; 82. the L-shaped block; 83. the rotating rods III; 84. the holding blocks; 85. the connecting gears; 86. the motor I; 90. the fixed casing I; 91. the drive rod I; 92. the rotating motor I; 93. the limit block I; 94. the fixed casing II; 95. the drive rod II; 96. the rotating motor II; 97. the limiting block II; 40. the spray pipes; 41. the clean water pipe; 42. the disinfection pipe; 43. the clean water tank; 44. the disinfection tank; 3f. the second vertical cylinder; 1a. the waste bag outlet; 1b. the isolation door; 1c. the electric telescopic rod I; 1d. the electric telescopic rod II; 1e. the display controller; 1f. the automatic waste bin 1f; 1g. the infrared detectors; 1h. the transparent glass cover.

5. SPECIFIC EMBODIMENT OF THE APPLICATION

To make the technical solutions provided by the invention more comprehensible, a further description of the invention is given below in combination with the attached drawings and embodiments, and the embodiments are exemplary and not the limitations of the scope of the disclosure. Apparently, the described drawings are merely some embodiments of the application rather than all the embodiments of the application. It should be understood that the application is not limited to the drawings described herein. Based on the drawings in the invention, all other drawings obtained by those of ordinary skill in the art without making creative labor fall within the scope of protection of the invention.

Figure 2:
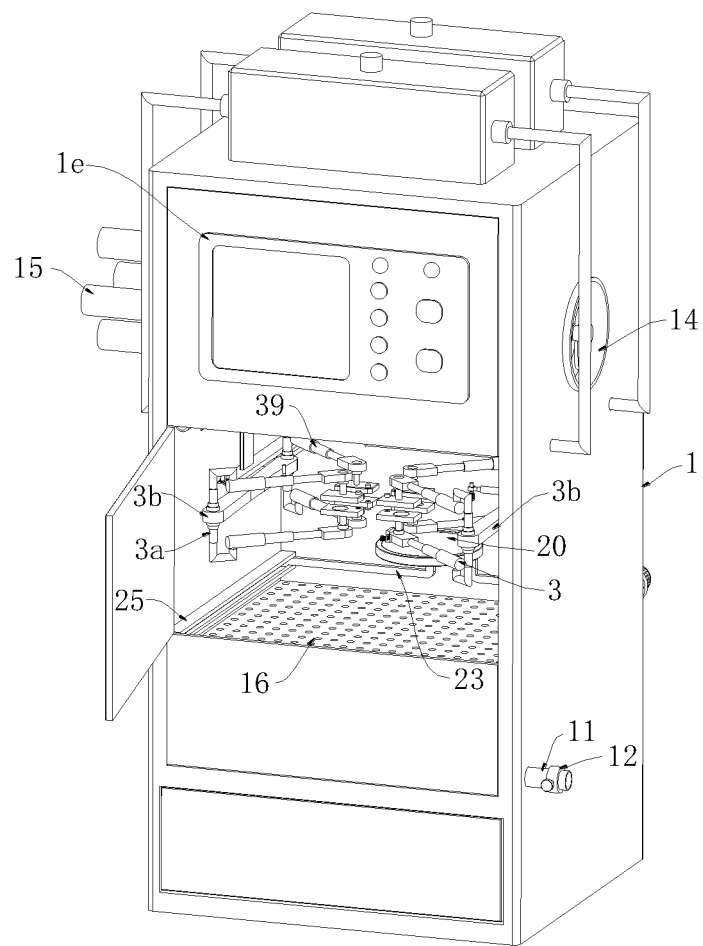
FIG. 2 is a schematic diagram showing the side view structure of part of the overall structure of the invention.
Figure 3:
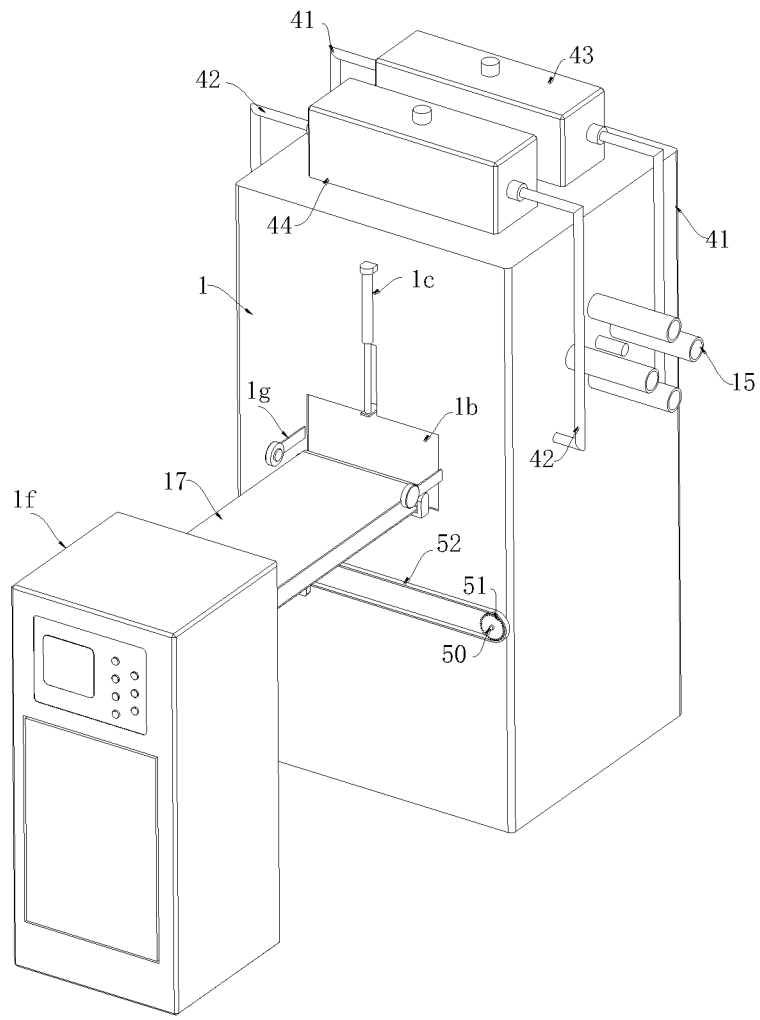
FIG. 3 is a schematic diagram I showing the rear-view structure of the invention.
Figure 4:
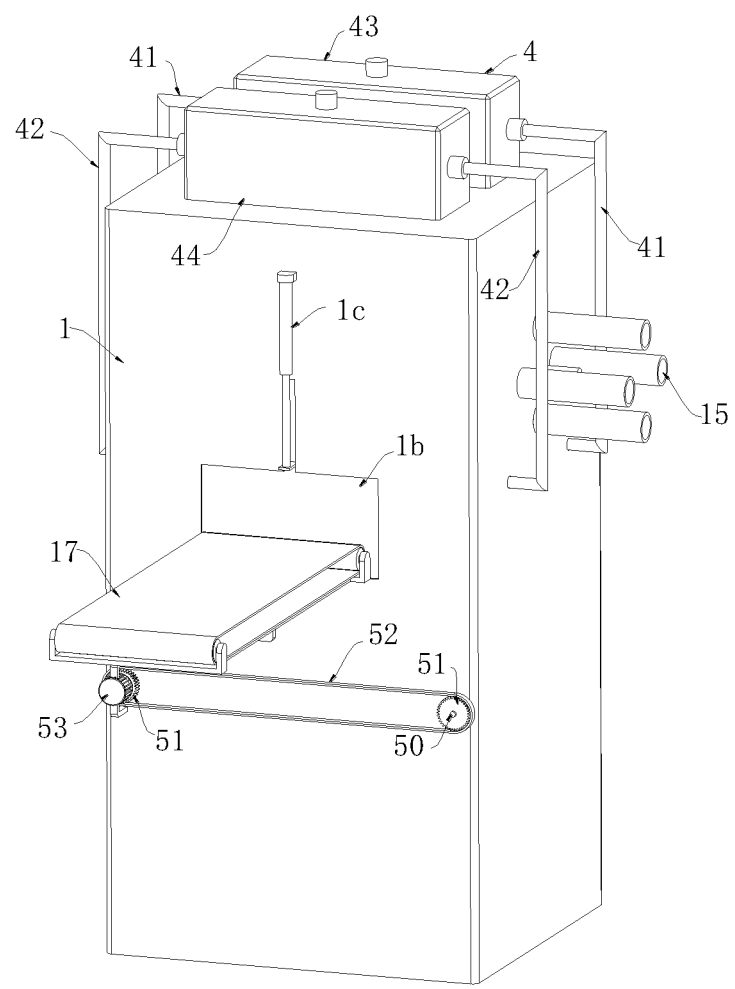
FIG. 4 is a schematic diagram II showing the rear-view structure of the structural part of the invention.
Figure 5:
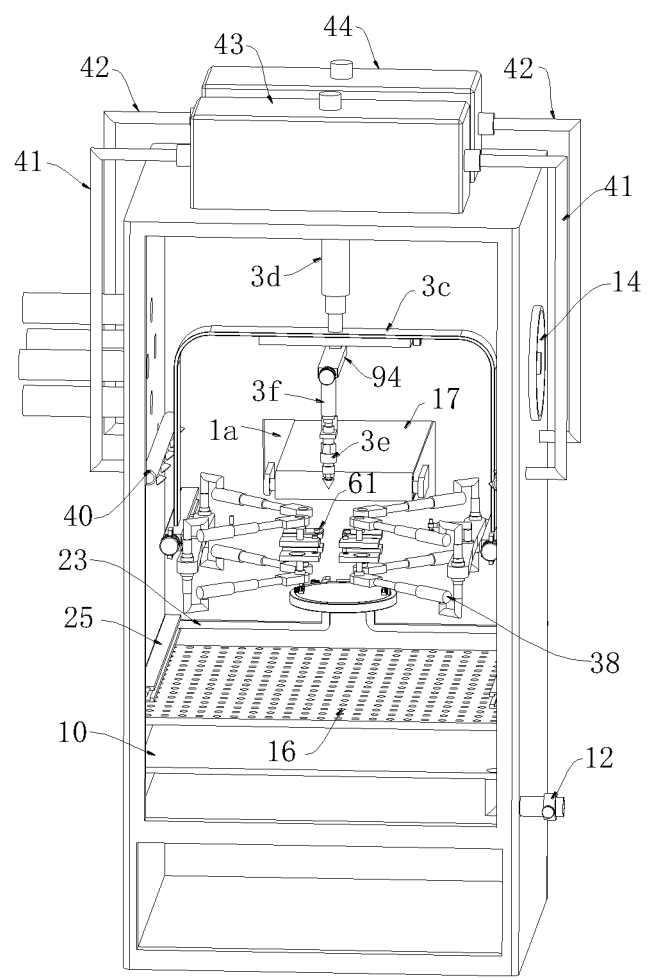
FIG. 5 is a schematic diagram I showing the internal structure of the invention in the main view.
Figure 6:
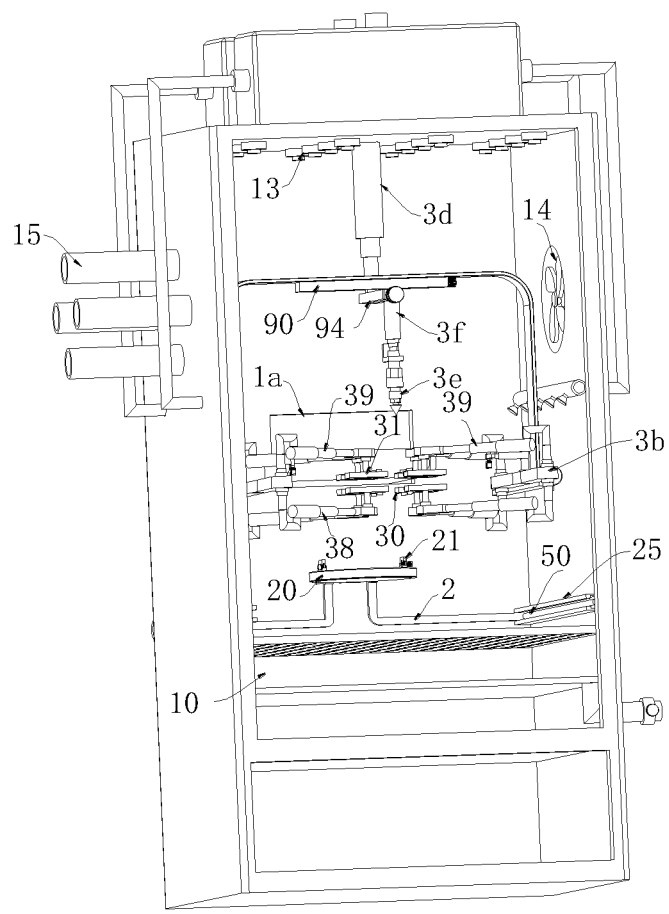
FIG. 6 is a schematic diagram II showing the internal structure of the invention in the main view.
Figure 7:
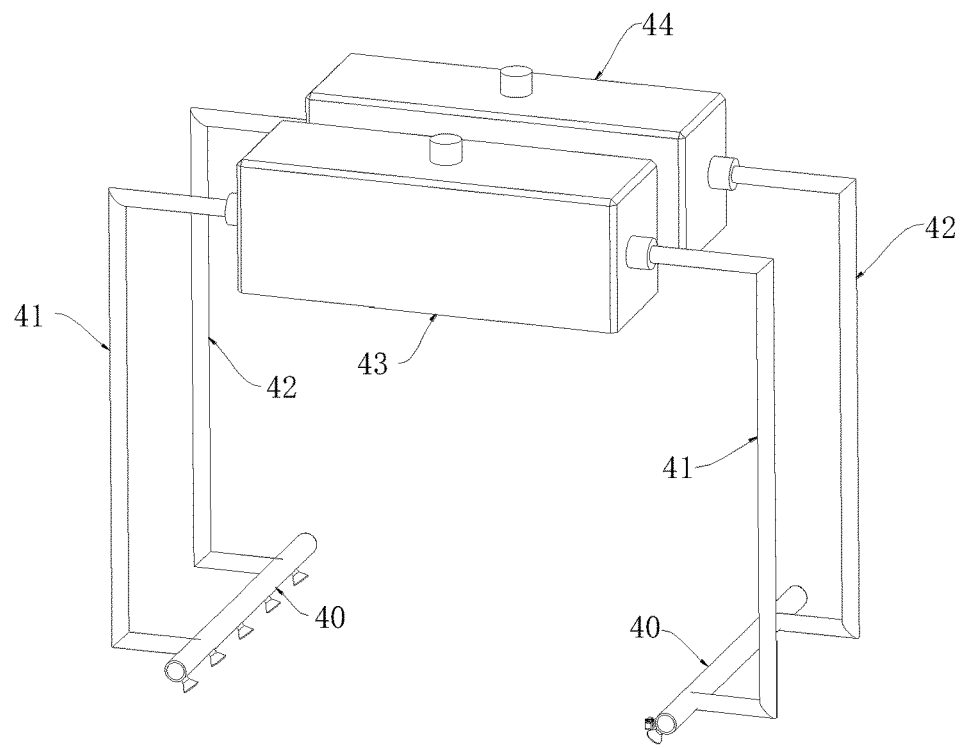
FIG. 7 is a schematic diagram showing the main view of the flushing and disinfection device of the invention.
Figure 8:
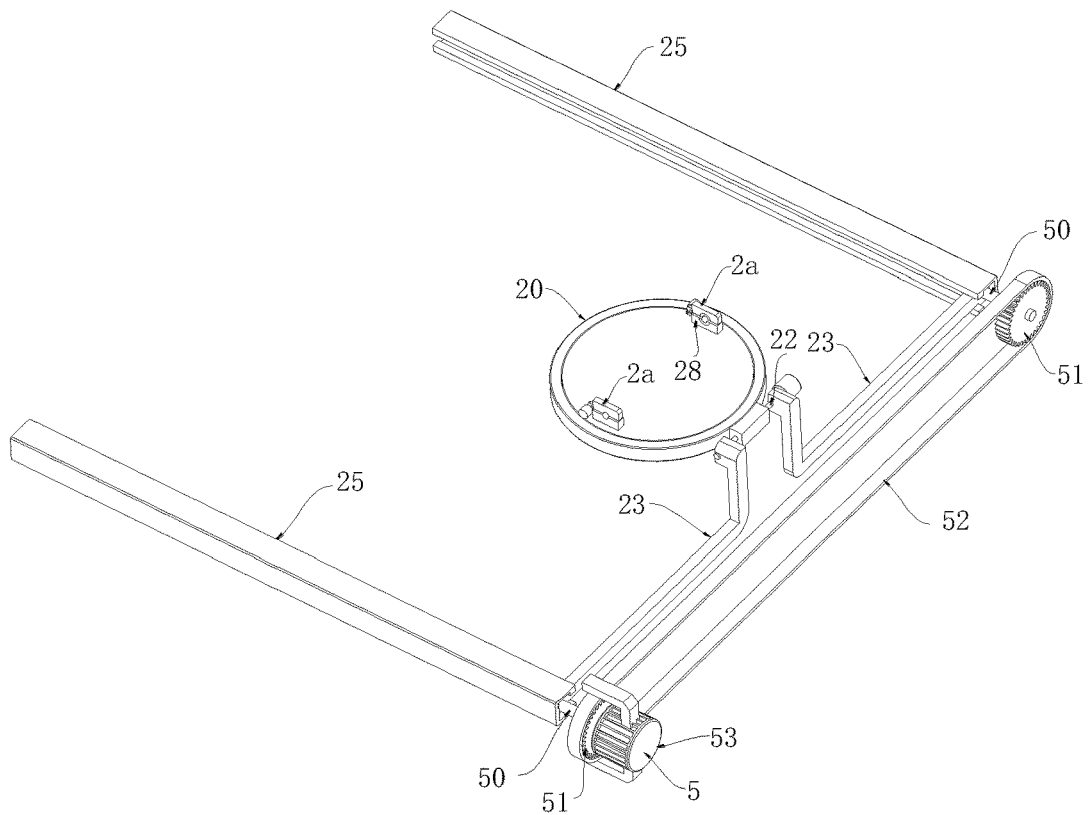
FIG. 8 is a schematic diagram showing the main view structure of the weighing device of the invention.
Figure 9:
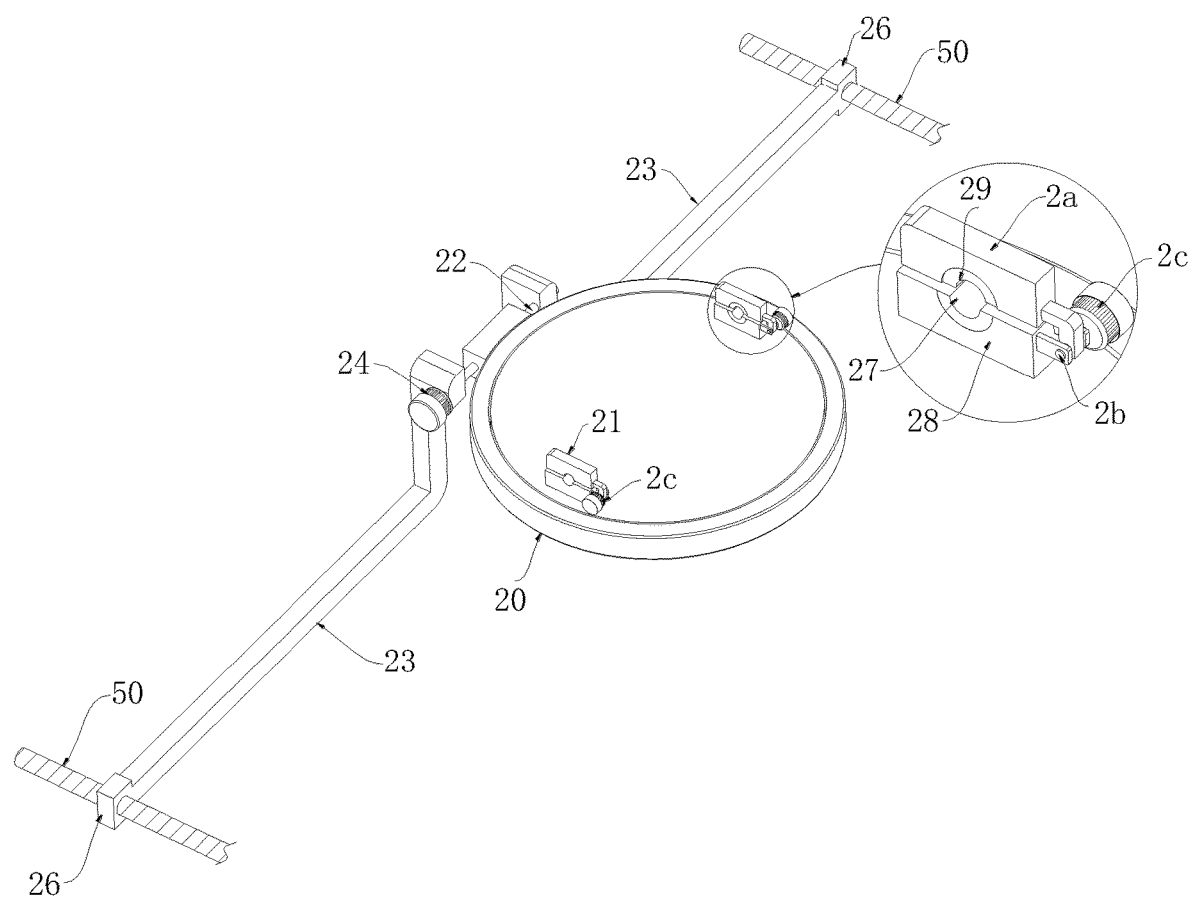
FIG. 9 is a schematic diagram showing the main view structure of part of the weighing device of the present invention.
Figure 10:
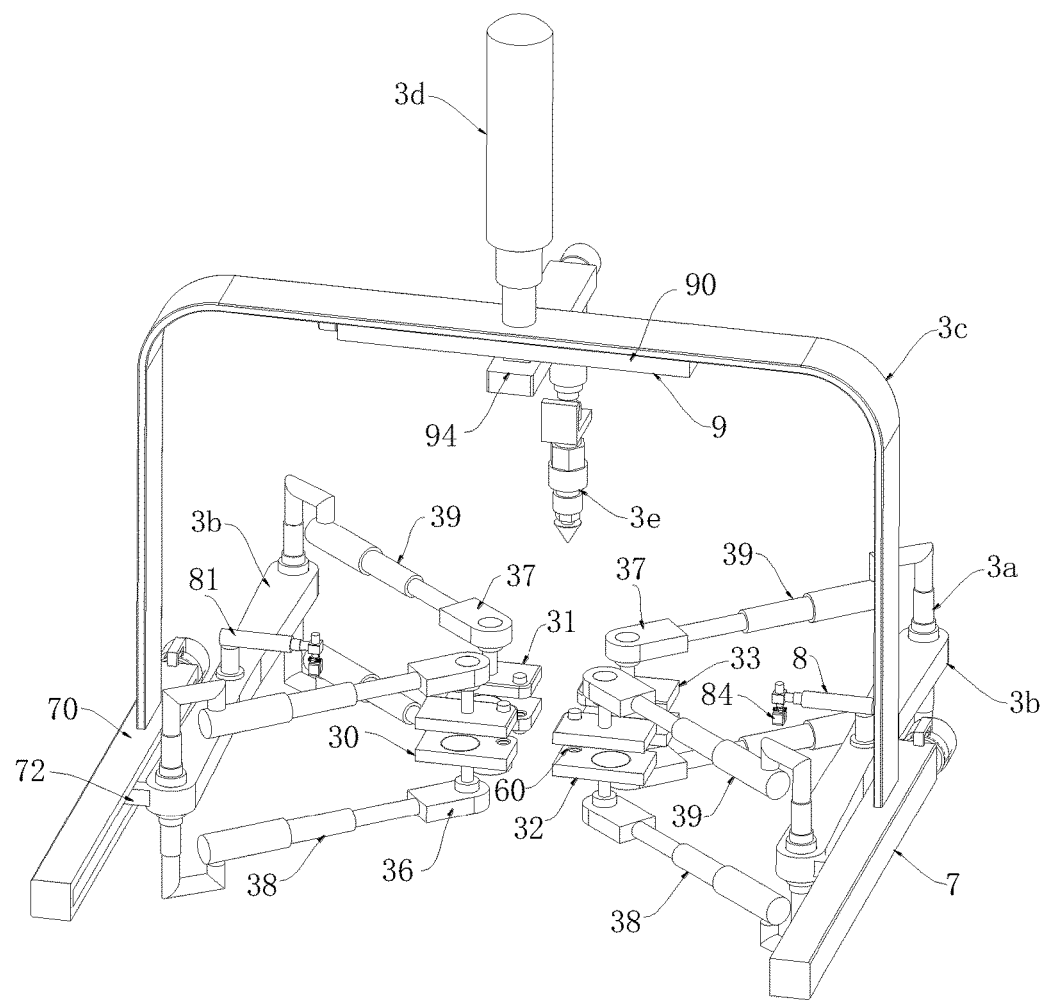
FIG. 10 is a schematic diagram showing the bottom view structure of the placing and cutting device of the invention.
Figure 11:
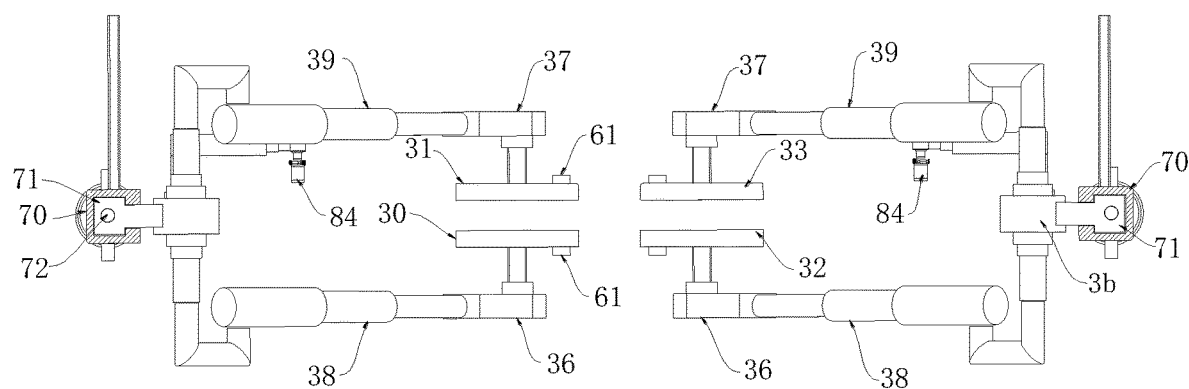
FIG. 11 is a schematic diagram showing the main view structure of the placing and cutting device of the invention.
Figure 12:
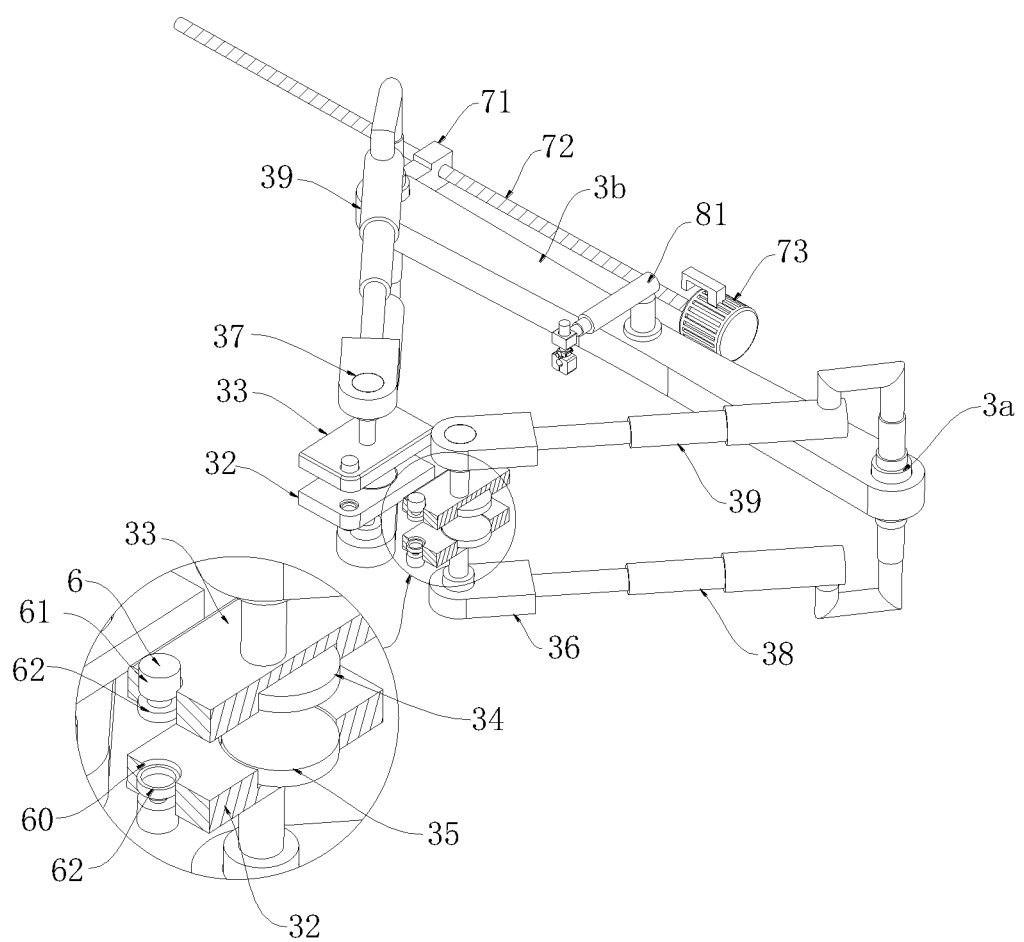
FIG. 12 is a schematic diagram showing the bottom fixed plate of the invention.
Figure 13:
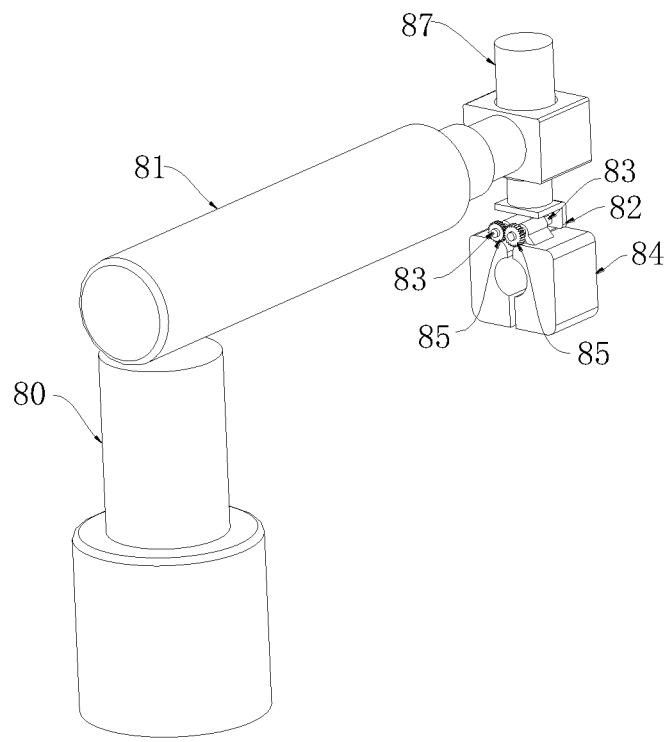
FIG. 13 is a schematic diagram showing the main view structure of the clamping assembly of the invention.
Figure 14:
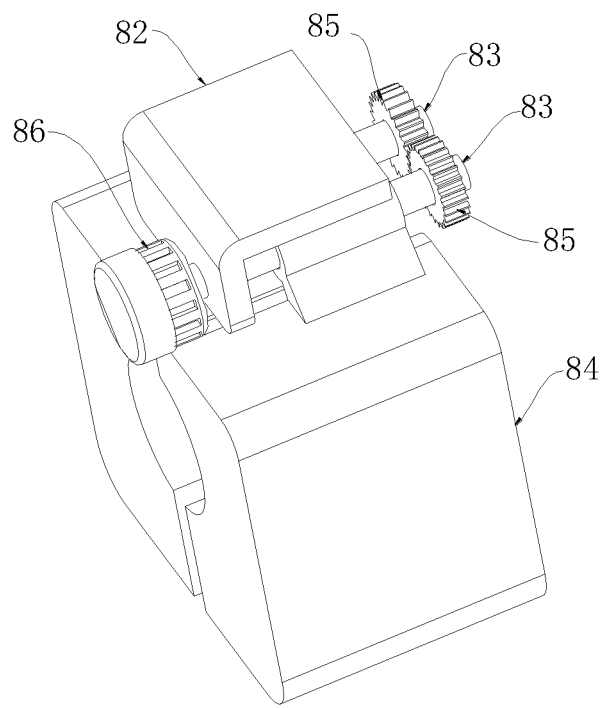
FIG. 14 is a schematic diagram showing the partial clamping assembly structure of the invention.
Figure 15:
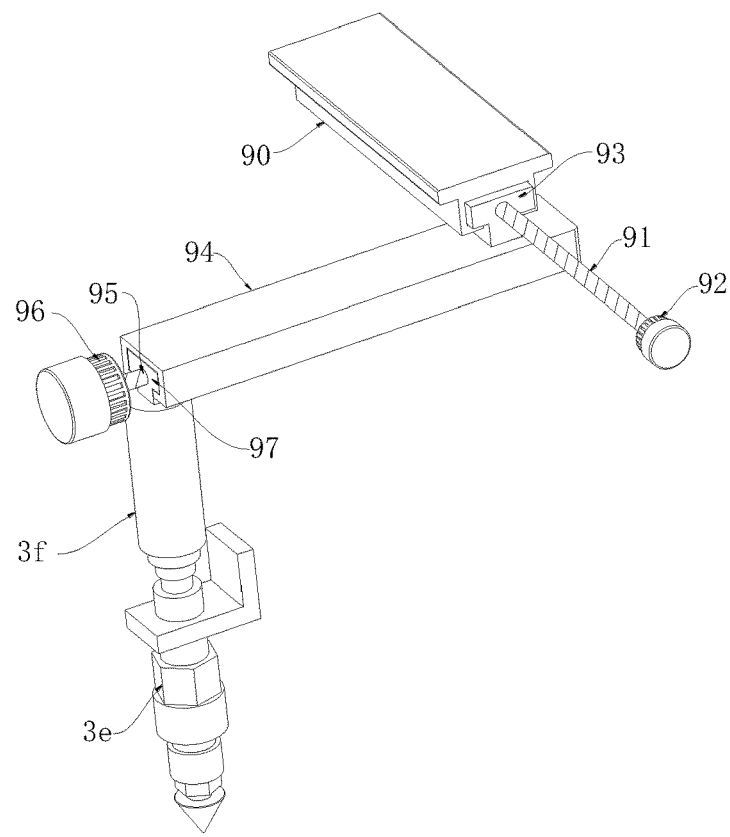
FIG. 15 is a schematic diagram showing a cross-sectional side view of the moving device of the invention.
Figure 16:
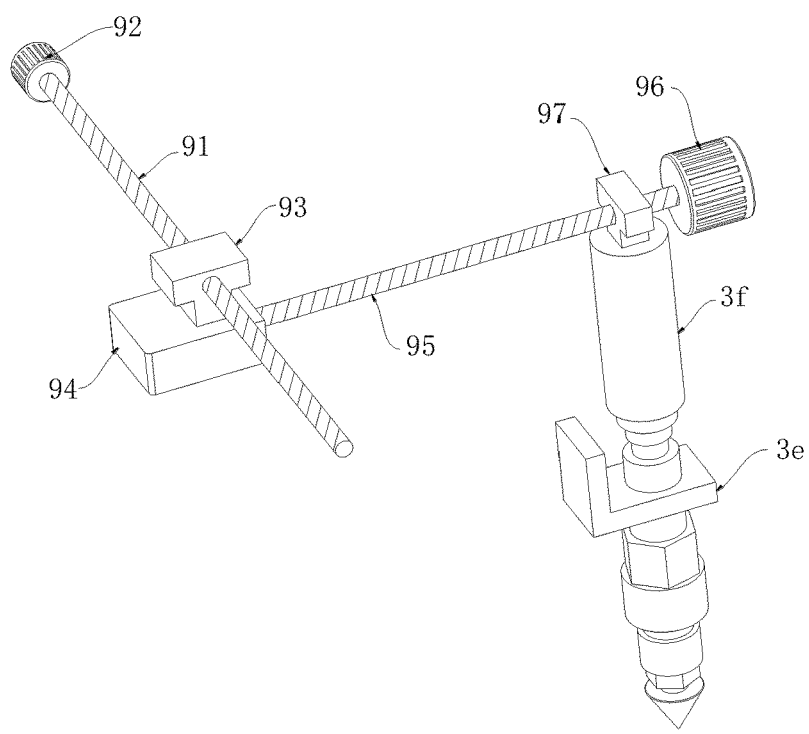
FIG. 16 is a schematic diagram showing the partially moving device structure of the invention.
Figure 17:
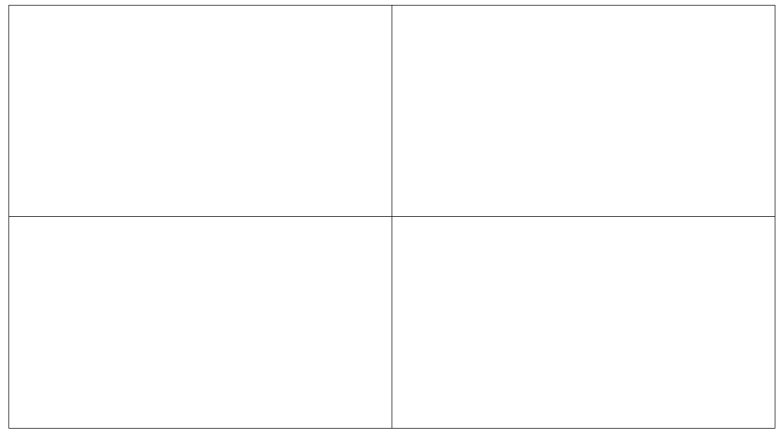
FIG. 17 is a schematic diagram showing the cut drainage bag of the invention.
Figure 18:
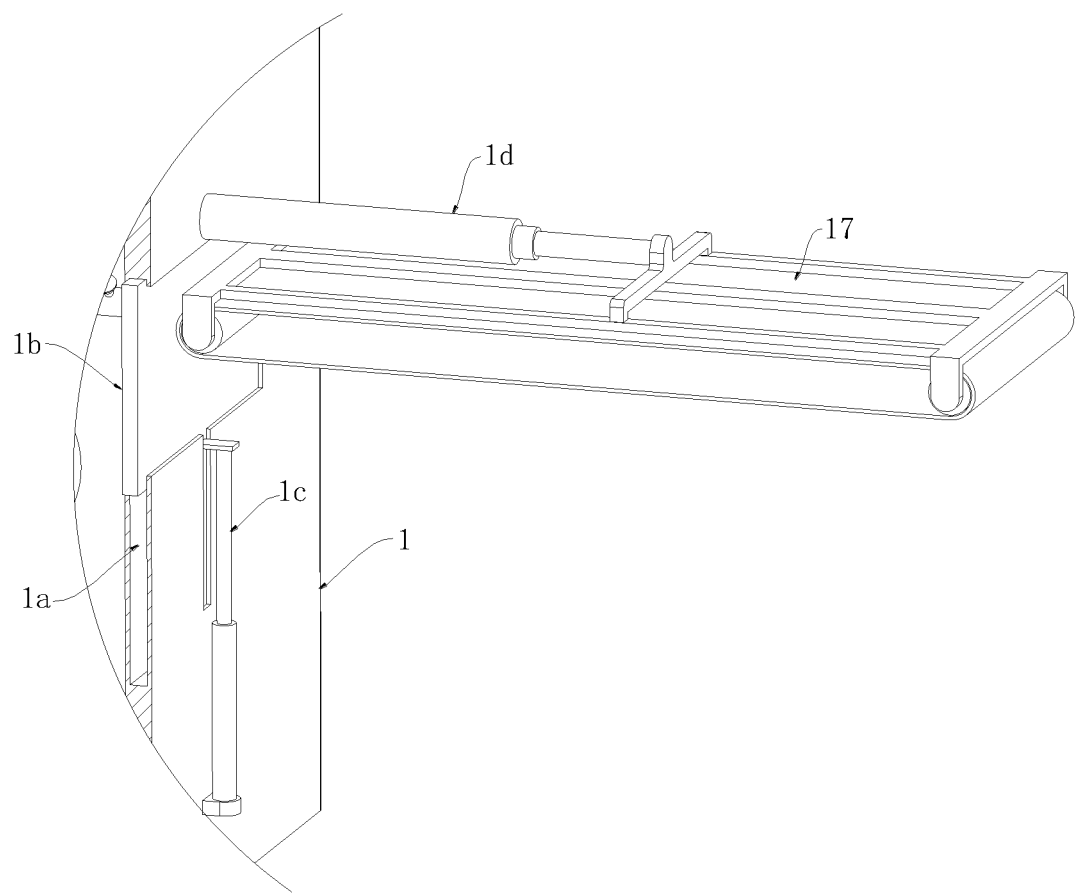
FIG. 18 is a schematic diagram showing the side view of the box main body of the invention.

Referring to FIG. 1-16, the invention provides a safe disposal machine for peritoneal dialysis liquid waste comprising a box main body 1, wherein the box main body 1 is provided with a liquid waste collection chamber 10 at the bottom, and the liquid waste collection chamber 10 is connected with a drainage pipe 11 at the bottom for drainage of the liquid waste, and the drainage pipe 11 is provided with a one-way valve 12, to prevent the backflow of odors above.

The interior of box main body 1 is provided with ultraviolet lamps 13 for disinfection of the interior of the box main body 1.

The box main body 1 is provided with a fan 14 on one side, and the box main body 1 is connected with ventilation ducts 15 for venting away from the fan 14.

The liquid waste collection chamber 10 is provided with a filter plate 16 on top, the filter plate 16 is provided with a weighing device 2 on top for weighing the peritoneal dialysis liquid waste, and the weighing device 2 is provided with a placing and cutting device 3 on top for cutting the drainage bag.

The box main body 1 is provided with a flushing and disinfection device 4 inside for disinfection of the drainage bags. The flushing and disinfection device 1 comprises spray pipes 40 provided on both sides of the inside of the box main body 1, and the spray pipes 40 are connected to the outside of the clear water pipe 41 and disinfection pipe 42; the box main body 1 is connected with a clear water tank 43 for placing clear water and a disinfection tank 44 for placing disinfection solution on the top, and the clear water pipe 41 and disinfection pipe 42 are connected with the clear water tank 43 and the disinfection tank 44 respectively.

The box main body 1 is provided with a waste bag outlet 1a on the outside, and an isolation door 1b is slidingly connected inside the waste bag outlet 1a; the isolation door 1b is connected with an electric telescopic rod I 1c on the top, and the electric telescopic rod I 1c is connected with the inside of the waste bag outlet 1a.

The box main body 1 is provided with a transmission belt 17 near the liquid waste bag outlet 1a, and the bottom of the transmission belt 17 is connected with an electric telescopic rod II 1d; the electric telescopic rod II 1d is provided at one end on the outside of the box main body 1, the transmission belt 17 is provided with an automatic waste bin 1f at one end, and one end of the transmission belt 17 is slidingly connected to the entrance of the automatic waste bin 1f; the transmission belt 17 is provided with infrared detectors 1g on both sides near the box main body 1, and the infrared detectors 1g are connected to the outer side of the box main body 1; the transmission belt 17 is provided with a transparent glass cover 1h on the outer side, and the two ends of the transparent glass cover 1h are connected to the box main body 1 and the automatic waste bin 1f respectively, to visualize the transfer of the liquid waste bag through the transparent glass cover 1h.

The automatic waste bin 1f is the existing technology, which can realize the function of fully automatic packing. When there are liquid waste bags on the transmission belt 17, the liquid waste bags can be detected by the infrared detector 1g, and the number of liquid waste bags detected by the infrared detector 1g can be displayed on the display controller 1e. Finally, the liquid waste bags will be transferred to the inside of the automatic waste bin 1f through the transmission belt 17. The automatic waste bin 1f can achieve automatic recycling, to avoid odor and easy splashing, and to facilitate the staff to count the number of liquid waste bags and clean the inside of the automatic waste bin 1f.

When in use, the drainage bag is first placed on weighing device 2, and then the end of the drainage pipe on the drainage bag near the drainage bag is clamped to weighing device 2. After placing the excessive length of the drainage bag and drainage pipe on both sides of the weighing device 2, and then closing the disinfection tank 44 door on box main body 1, the drainage bag can be weighed.

When the weighing is complete, placing and cutting device 3 can be removed from weighing device 2, and the drainage bag and drainage pipe can be fixed. And the drainage pipe is in the middle line of the drainage bag, allowing the drainage bag and the drainage bag drainage pipe to be cut. And the fan 14 starts to open while the placing and cutting device is cutting the drainage bag until the liquid waste bag is cleaned and disinfected and transferred out through the transmission belt 17. The air inside box main body 1 can be discharged from ventilation pipe 15 under the action of the fan 14 to discharge the odor inside the box main body 1, and to blow dry the residual water stains inside the box main body 1. In addition to removing the exhaust gas, the fan 14 can also blow dry the liquid remaining inside the box after the liquid waste bag is output from the box to keep the final dry and clean inside the box main body 1. The fan 14 can be pre-set to work for about 1-2 minutes after the output of the liquid waste bag to facilitate better aeration of the interior of the box main body 14. Moreover, the fan 14 has a waterproof function, and there should be a net cover set in front of fan 14 to prevent the liquid waste bag from touching the fan blade and affecting the normal work of the fan blade.

When placing and cutting equipment 3 to cut the drainage bag and drainage bag drainage pipe, placing and cutting equipment 3 can also drive the cut drainage bag to move, which can make the cut drainage bag turn over. Then the flushing and disinfection device 4 can be opened, and the flushing and disinfection device 4 can flush and disinfect the drainage bag. When the disinfection of the drainage bag is completed, the electric telescopic rod I 1c is opened, and the electric telescopic rod I 1c drives the isolation door 1b to open. At the same time, the electric telescopic rod II 1d is opened, and the electric telescopic rod II 1d drives one end of the transmission belt through the waste bag outlet 1a into the interior of box main body 1. Then placing and cutting device 3, can place the flushed and disinfected drainage bag to the transmission belt 17. Then the electric telescopic rod II 1d drives the transmission belt 17 and the drainage bag to move out of the outer side of the box main body 1, and the isolation door 1b is closed, and then the disinfected liquid waste bag driven by the transmission belt 17 can enter the inside of the medical waste garbage bag.

When the liquid waste bag is transferred out of the box main body 1 and the isolation door 1b is closed, then the ultraviolet lamps 13 are turned on to sterilize the interior of the box main body 1 as a whole to prevent the spread of the infectious liquid waste.

The flushed liquid waste is transferred to the inside of the liquid waste collection chamber 10 through the filter plate 16 and thus discharged from the drainage pipe 11, and the bottom of the liquid waste collection chamber 10 is provided with an inclined shape, which can facilitate the discharge of the liquid waste from the drainage pipe 11 more easily.

The outside of the box main body 1 is provided with a display controller 1e, to control the work of the weighing device. It also has a detachment function, to ensure the accuracy of the weighing. At the same time, the display controller 1c can also display the working status of the box, and the display controller 1e is equipped with an indicator light, with the indicator light on when the box main body 1 is working.

At the same time, the display controller is connected to the fan 14, ultraviolet lamps 13, and disinfection device 4, to control the operation of the device and display the working status of the fan 14, ultraviolet lamps 13, and disinfection device 4, as well as the working countdown.

The display controller 1c is provided with an on/off button, allowing all devices to stop working when closed to safely open the box door and ensure the safety of operation.

The fixed mechanism 21 comprises a pressure plate I 28 provided at the top ends of the weigher 20 with a clamping hole I 27, and the pressure plate I 28 is provided with a pressure plate II 2a with a clamping hole II 29 at the top; the pressure plate II 2a is provided with a rotating rod II 2b on the outside, the rotating rod II 2b is connected to the outside of pressure plate I 28 by rotation at both ends, and one end of the rotating rod II 2b is connected to a drive motor III 2c through pressure plate I 28, and the drive motor III 2c is fixed to the outside of pressure plate I 28 by a waterproof cover.

The weigher 20 is provided with a rotating rod I 22 on the outside, and the rotating rod I 22 is rotatingly connected to L-shaped plates 23 on both sides; the rotating rod I 22 is connected to drive motor I 24 through L-shaped plates 23 at one end, and drive motor I 24 is fixed to the outside of L-shaped plates 23 through a waterproof cover.

The box main body 1 is provided with supporting casings I 25 on both sides inside, the supporting casings I 25 is slidingly connected with supporting block I 26 inside, and the supporting block I 26 is connected to one end of the L-shaped plate 23 on the outside.

The supporting casing I 25 is provided with a drive assembly 5 inside for driving the supporting block I 26 to move.

The drive assembly 5 comprises screw rods 50 rotatably connected to the inside of the supporting casings I 25, and the screw rods 50 are connected to the supporting block I 26; one end of the screw rods 50 is connected to drive gears 51 through the box main body 1, and two drive gears 51 are connected in mesh with a gear link 52; either one of the screw rods 50 is connected to drive motor II 53 through drive gear 51, and drive motor II 53 is fixed to the outside of the box main body 1 through a waterproof cover.

When in use, the drive motor II 53 drives the screw rods 50 to rotate, and the screw rods 50 drive the supporting block I 26 to move. The supporting block I 26 drives the L-shaped plates 23 to move, and the L-shaped plates 23 drive the rotating rod I 22 and the drive motor I 24 to move. The rotating rod I 22 can drive the weigher 20 to move to a position close to the door of the disinfection tank 44. The medical personnel then place the drainage bag onto the weigher 20, while placing the end of the drainage pipe near the drainage bag inside the clamping hole I 27 and the clamping hole II 29, and then the drive motor III 2c drives the pressure plate II 2a to rotate to achieve the fixation of one end of the drainage pipe of the drainage bag.

The screw rods 50 drive the weigher 20 to move to the inside of the box main body 1, and after closing the door of the disinfection tank 44, the weigher 20 can weigh the drainage bag, and after the weighing is completed, the drainage bag can be removed from the weigher 20 by placing and cutting device 3.

When not in use, the drive motor 24 drives the rotating rod I 22 to lift the weigher 20 up, saving the internal space of the box main body 1.

The placing and cutting device 3 comprises a bottom support plate set 30 and a top support plate set 31 provided at the top of the weigher 20, allowing the top and bottom of the drainage bag to be fixed respectively; the bottom support plate set 30 and top support plate set 31 consist of a plurality of bottom fixed plates 32 and top fixed plates 33, respectively.

The bottom fixed plates 32 are connected with electromagnets 34 at the top and the top fixed plates 33 are connected with iron sheets 35 corresponding to electromagnets 34 at the bottom; the bottom fixed plates 32 and bottom fixed plates 32 are connected with adsorption mechanisms 6 at the ends close to each other for adsorbing the split portion of the drainage bag.

The adsorption mechanism 6 comprises fixed grooves 60 provided on the bottom fixed plates 32, and micro cylinders I 61 are provided inside the fixed grooves 60, and the output end of the micro cylinders I 61 is connected to vacuum chucks 62 for adsorption on the cut drainage bags.

The bottom fixed plates 32 at the bottom and top fixed plates 33 at the top are connected with connection plates I 36 and connection plates II 37, respectively; the connection plates I 36 and II 37 are connected on one side with telescopic cylinders I 38 and telescopic cylinders II 39 respectively, and the telescopic cylinders I 38 and II 39 near each other are connected at one end with double-head cylinders 3a; the double-head cylinders 3a on one side are connected to moving plates 3b, and the box main body 1 is provided with moving devices 7 on each side of the interior of the box main body 1 for moving the two moving plates 3b respectively.

The mobile devices 7 comprise supporting casings II 70 provided inside the box main body 1, and the supporting cases II 70 are internally slidingly connected with supporting blocks II 71; the supporting casings II 70 are internally rotationally connected with a threaded rod 72, and the threaded rod 72 is connected to the supporting block II 71; the threaded rod 72 through the supporting casings II 70 is connected to the drive motor IV 73, and the drive motor IV 73 is fixed to the outside of the supporting casings II 70 through the waterproof cover.

Two moving devices 7 are connected at the top with a U-shaped plate 3c, and the U-shaped plate 3c is connected at the top with a first vertical cylinder 3d, and the first vertical cylinder 3d is connected to the top interior of the box main body 1.

The clamping assembly 8 comprises a fixed rod I 80 provided at the top of the moving plates 3b, and an output cylinder 81 is provided at the top of the fixed rod I 80; the output end of the output cylinder 81 is connected to a micro cylinder II 87, and the output of the micro cylinder II 87 is connected to an L-shaped block 82; the L-shaped block 82 is connected with two rotating rods III 83 on the inner side, and both the rotating rods III 83 are connected with holding blocks 84 for holding the drainage bag and drainage pipe; the rotating rod II 83 is provided with connecting gears 85, and the two connecting gears 85 are connected in mesh; any of the rotating rods III 83 is connected to motor I 86, and motor I 86 is fixed to the outside of the L-shaped block 82 by a waterproof cover.

The top supporting plate set 31 is provided with a waterjet 3e for cutting the drainage bag at the top, the waterjet 3e is provided with a moving assembly 9 for driving the waterjet 3e to move at the top, and the moving assembly 9 is connected to the bottom of the U-shaped plate 3c.

The moving assembly 9 comprises a fixed casing I 90 provided at the bottom of the U-shaped plate 3c, and the fixed casing I 90 is internally in a rotating connection with a threaded drive rod I 91; the drive rod I 91 is connected to a rotating motor I 92 through one end of the fixed casing I 90, and the rotating motor I 92 is fixed to the outside of the fixed casing I 90 by a waterproof cover.

The fixed casing I 90 is internally in the sliding connection with limit block I 93, and limit block I 93 is connected with drive rod I 91; the limit block I 93 is connected with fixed casing II 94 at the bottom, and fixed casing II 94 is internally in the rotating connection with threaded drive rod II 95, and drive rod II 95 is connected with rotating motor II 96 through fixed casing II 94 at one end.

The drive rod II 95 is externally connected to the limit block II 97, and the limit block II 97 is slidingly connected to the inside of the fixed casing II 94; the limit block II 97 is connected to the second vertical cylinder 3f at the bottom, and the output end of the second vertical cylinder 3f is connected to the top of the waterjet 3c.

When the weigher 20 finishes weighing the drainage bag, the four telescopic cylinders II 39 drive the four connection plates II 37 and the four top fixing plates 33 to move to the top of the drainage bag respectively. The top of the double-head cylinders 3a drives the four top fixed plates to move to the top of the drainage bag, and then the micro cylinders I 61 on the top fixed plates 33 are opened. The micro cylinders I 61 drive the vacuum chuck 62 to move out from inside the fixed grooves 60 to adsorb the top of the drainage bag, and then the screw rods 50 drive the weigher 20 to move out from the bottom of the drainage bag.

At the same time the pressure plate II 2a is opened, and then the output cylinder 81 and the micro cylinder II 87 are opened, allowing the two clamping blocks to be located on the outer side of the drainage pipe of the drainage bag. Then the motor I 86 is turned on, and the motor I 86 drives the two rotating rods III 83 and the two connecting gears 85 to rotate, and the two rotating rods drive the two clamping blocks to rotate, then the two ends of the drainage pipe of the drainage bag can be clamped.

Finally, the drive motor II 53 and the screw rods 50 are started, and the screw rods 50 drive the weigher 20 to move out from the bottom of the drainage bag. At the same time, the telescopic cylinders I 38 are turned on, and the telescopic cylinders I 38 drive the bottom fixed plate 32 to move to the bottom of the drainage bag. The micro cylinders I 61 on the bottom fixed plate 32 are opened at the same time, allowing the chuck on the bottom fixed plate 32 to adsorb to the bottom of the drainage bag.

The electromagnets 34 are energized and can be used in conjunction with the iron sheets 35 to fix the drainage bag and avoid the drainage bag from moving during cutting.

When the weigher 20 finishes weighing the drainage bag, the four telescopic cylinders II 39 drive the four connection plates II 37 and the four top fixing plates 33 to move to the top of the drainage bag respectively. The top of the double-head cylinders 3a drives the four top fixed plates to move to the top of the drainage bag, and then the micro cylinders I 61 on the top fixed plates 33 are opened. The micro cylinders I 61 drive the vacuum chuck 62 to move out from inside the fixed grooves 60 to adsorb the top of the drainage bag, and then the screw rods 50 drive the weigher 20 to move out from the bottom of the drainage bag.

Then the rotating motor I 92 is turned on and the rotating motor I 92 can drive the drive rod I 91 to rotate. The drive rod I 91 drives the limit block I 93 to move, and the limit block I 93 drives the fixed casing II 94 to move. Fixed casing II 94 drives limit block II 97 to move, and limit block II 97 can drive the waterjet 3e lateral movement along the middle line of the drainage bag, allowing the cutting of the drainage pipe of the drainage bag. Then the rotating motor II 96 is turned on, and the rotating motor II 96 drives the drive rod II 95 to rotate. Drive rod II 95 drives the waterjet 3c longitudinal movement along the longitudinal center line of the drainage bag to achieve the longitudinal cutting of the drainage, allowing the drainage bag to be cut into the shape of a cross. During the longitudinal cutting, the waterjet 3e moves to the position where it intersects with the transverse cutting without cutting, to avoid cutting the drainage pipe of the drainage bag.

When the cutting is completed, four telescopic cylinders I 38 and four telescopic cylinders II 39 can drive the bottom fixed plate 32 and four top fixed plate 33 and vacuum chuck 62 to move. At the same time, the electromagnets 34 are de-energized, allowing the top vacuum chuck 62 and the bottom vacuum chuck 62 to drive the top and bottom corners of the cross-cut drainage bag to move and flip open for flushing and disinfection by the spray pipes 40. When flushing, the water tank 43 connected to the spray pipes 40 needs to be opened first, to perform flushing. Then the disinfection tank 44 connected to the spray pipes 40 is opened, enabling the disinfection solution to be sprayed out and the drainage bag to be disinfected.

The box main body 1 of the invention is provided with existing protective equipment, and the protective equipment can protect the internal wire connection safety, housing leakage protection, fuse and electric fusion end safety, and electric breakdown strength safety of the box. Once there is leakage and other conditions inside the box main body 1, the protection equipment on the box main body 1 will automatically power off and alarm. Such boxes 1 with protection equipment are available in the prior art; therefore, the invention is not specifically illustrated.

In the invention, drive motor I 24, drive motor II 53, drive motor III 2c and drive motor IV 73 are in preference to the Y80M1-2 model. Rotating motor I 92 and rotating motor II 96 are in preference to model Y80M2-2. Circuit operation is the existing conventional circuit, and the circuit as well as control involved in the invention are all prior art and will not be repeated in detail here.

It should be noted that herein, relational terms such as 'first' and 'second' are used merely to an entity or operation are distinguished with another entity or operation, without necessarily requiring or implying that these entities or operation have any actual relationship or order or sequence. Moreover, the term 'comprise' or 'contain' or any of their variants are to be taken in their non-exclusive sense. Thus, processes, methods, merchandise, or equipment that comprises a series of elements not only comprises those elements, but also comprises other elements that have not been explicitly listed or elements that are intrinsic to such processes, methods, merchandise, or equipment.

What should be finally explained is that although the embodiments of the invention have been shown and described above, the above embodiments are exemplary and not the limitations, and without deviating from the spirit and scope of the technical scheme in the invention, other changes, modifications, replacements and variations on the technical scheme in the invention can be made by common technicians in the field.

The invention claimed is:
1. A safe disposal machine for peritoneal dialysis liquid waste comprises a box main body (1), wherein: the box main body (1) is provided with a liquid waste collection chamber (10) at the bottom, and the liquid waste collection chamber (10) is connected with a drainage pipe (11) at the bottom for drainage of the liquid waste, and the drainage pipe (11) is provided with a one-way valve (12);

the interior of box main body (1) is provided with ultraviolet lamps (13) for disinfection of the interior of the box main body (1);

the box main body (1) is provided with a fan (14) on one side, and the box main body (1) is connected with ventilation ducts (15) for venting away from the fan (14);

the liquid waste collection chamber (10) is provided with a filter plate (16) on top, the filter plate (16) is provided with a weighing device (2) on top for weighing the peritoneal dialysis liquid waste, and the weighing device (2) is provided with a placing and cutting device (3) on top for cutting the drainage bag;

the box main body (1) is provided with a flushing and disinfection device (4) inside for disinfection of the drainage bags;

the box main body (1) is provided with a waste bag outlet (1a) on the outside, and an isolation door (1b) is slidingly connected inside the waste bag outlet (1a); the isolation door (1b) is connected with an electric telescopic rod I (1c) on the top, and the electric telescopic rod I (1c) is connected with the inside of the waste bag outlet (1a);

the box main body (1) is provided with a transmission belt (17) near the liquid waste bag outlet (1a), and the bottom of the transmission belt (17) is connected with an electric telescopic rod II (1d); the electric telescopic rod II (1d) is provided at one end on the outside of the box main body (1), the transmission belt (17) is provided with an automatic waste bin (1f) at one end, and one end of the transmission belt (17) is slidingly connected to the entrance of the automatic waste bin (1f); the transmission belt (17) is provided with infrared detectors (1g) on both sides near the box main body (1), and the infrared detectors (1g) are connected to the outer side of the box main body (1); the transmission belt (17) is provided with a transparent glass cover (1h) on the outer side, and the two ends of the transparent glass cover (1h) are connected to the box main body (1) and the automatic waste bin (1f) respectively;

the weighing device (2) comprises a weigher (20) provided at the bottom of the box main body (1), and the weigher (20) is provided with a fixed mechanism (21) at the top for fixing the drainage bag and drainage pipe;

the weigher (20) is provided with a rotating rod I (22) on the outside, and the rotating rod I (22) is rotatingly connected to L-shaped plates (23) on both sides; the rotating rod I (22) is connected to drive motor I (24) through L-shaped plates (23) at one end, and drive motor I (24) is fixed to the outside of L-shaped plates (23) through a waterproof cover;

the box main body (1) is provided with supporting casings I (25) on both sides inside, the supporting casings I (25) is slidingly connected with supporting block I (26) inside, and the supporting block I (26) is connected to one end of the L-shaped plate (23) on the outside;

the supporting casing I (25) is provided with a drive assembly (5) inside for driving the supporting block I (26) to move;

the placing and cutting device (3) comprises a bottom support plate set (30) and a top support plate set (31) provided at the top of the weigher (20), allowing the top and bottom of the drainage bag to be fixed respectively; the bottom support plate set (30) and top support plate set (31) consist of a plurality of bottom fixed plates (32) and top fixed plates (33), respectively;

the bottom fixed plates (32) are connected with electromagnets (34) at the top and the top fixed plates (33) are connected with iron sheets (35) corresponding to electromagnets (34) at the bottom; the bottom fixed plates

(32) and bottom fixed plates (32) are connected with adsorption mechanisms (6) at the ends close to each other for adsorbing the split portion of the drainage bag;

the bottom fixed plates (32) at the bottom and top fixed plates (33) at the top are connected with connection plates I (36) and connection plates II (37), respectively; the connection plates I (36) and II (37) are connected on one side with telescopic cylinders I (38) and telescopic cylinders II (39) respectively, and the telescopic cylinders I (38) and II (39) near each other are connected at one end with double-head cylinders (3a); the double-head cylinders (3a) on one side are connected to moving plates (3b), and the box main body (1) is provided with moving devices (7) on each side of the interior of the box main body (1) for moving the two moving plates (3b) respectively; two moving devices (7) are connected at the top with a U-shaped plate (3c), and the U-shaped plate (3c) is connected at the top with a first vertical cylinder (3d), and the first vertical cylinder (3d) is connected to the top interior of the box main body (1);

the moving plates (3b) are provided with a clamping assembly (8) on top for clamping the drainage bag and drainage pipe;

the top supporting plate set (31) is provided with a waterjet (3e) for cutting the drainage bag at the top, the waterjet (3e) is provided with a moving assembly (9) for driving the waterjet (3e) to move at the top, and the moving assembly (9) is connected to the bottom of the U-shaped plate (3c).

2. A safe disposal machine for peritoneal dialysis liquid waste according to claim 1, wherein the drive assembly (5) comprises screw rods (50) rotatably connected to the inside of the supporting casings I (25), and the screw rods (50) are connected to the supporting block I (26); one end of the screw rods (50) is connected to drive gears (51) through the box main body (1), and two drive gears (51) are connected in mesh with a gear link (52); either one of the screw rods (50) is connected to drive motor II (53) through drive gear (51), and drive motor II (53) is fixed to the outside of the box main body (1) through a waterproof cover.

3. A safe disposal machine for peritoneal dialysis liquid waste according to claim 1, wherein the fixed mechanism (21) comprises a pressure plate I (28) provided at the top ends of the weigher (20) with a clamping hole I (27), and the pressure plate I (28) is provided with a pressure plate II (2a) with a clamping hole II (29) at the top; the pressure plate II (2a) is provided with a rotating rod II (2b) on the outside, the rotating rod II (2b) is connected to the outside of pressure plate I (28) by rotation at both ends, and one end of the rotating rod II (2b) is connected to a drive motor III (2c) through pressure plate I (28), and the drive motor III (2c) is fixed to the outside of pressure plate I (28) by a waterproof cover.

4. A safe disposal machine for peritoneal dialysis liquid waste according to claim 1, wherein the adsorption mechanism (6) comprises fixed grooves (60) provided on the bottom fixed plates (32), and micro cylinders I (61) are provided inside the fixed grooves (60), and the output end of the micro cylinders I (61) is connected to vacuum chucks (62) for adsorption on the cut drainage bags.

5. A safe disposal machine for peritoneal dialysis liquid waste according to claim 1, wherein the mobile devices (7) comprise supporting casings II (70) provided inside the box main body (1), and the supporting cases II (70) are internally slidingly connected with supporting blocks II (71); the supporting casings II (70) are internally rotationally connected with a threaded rod (72), and the threaded rod (72) is connected to the supporting block II (71); the threaded rod (72) through the supporting casings II (70) is connected to the drive motor IV (73), and the drive motor IV (73) is fixed to the outside of the supporting casings II (70) through the waterproof cover.

6. A safe disposal machine for peritoneal dialysis liquid waste according to claim 1, wherein the clamping assembly (8) comprises a fixed rod I (80) provided at the top of the moving plates (3b), and an output cylinder (81) is provided at the top of the fixed rod I (80); the output end of the output cylinder (81) is connected to a micro cylinder II (87), and the output of the micro cylinder II (87) is connected to an L-shaped block (82); the L-shaped block (82) is connected with two rotating rods III (83) on the inner side, and both the rotating rods III (83) are connected with holding blocks (84) for holding the drainage bag and drainage pipe;

the rotating rod III (83) is provided with connecting gears (85), and the two connecting gears (85) are connected in mesh; any of the rotating rods III (83) is connected to motor I (86), and motor I (86) is fixed to the outside of the L-shaped block (82) by a waterproof cover.

7. A safe disposal machine for peritoneal dialysis liquid waste according to claim 1, wherein the moving assembly (9) comprises a fixed casing I (90) provided at the bottom of the U-shaped plate (3c), and the fixed casing I (90) is internally in a rotating connection with a threaded drive rod I (91); the drive rod I (91) is connected to a rotating motor I (92) through one end of the fixed casing I (90), and the rotating motor I (92) is fixed to the outside of the fixed casing I (90) by a waterproof cover;

the fixed casing I (90) is internally in the sliding connection with limit block I (93), and limit block I (93) is connected with drive rod I (91); the limit block I (93) is connected with fixed casing II (94) at the bottom, and fixed casing II (94) is internally in the rotating connection with threaded drive rod II (95), and drive rod II (95) is connected with rotating motor II (96) through fixed casing II (94) at one end;

the drive rod II (95) is externally connected to the limit block II (97), and the limit block II (97) is slidingly connected to the inside of the fixed casing II (94); the limit block II (97) is connected to the second vertical cylinder (30 at the bottom, and the output end of the second vertical cylinder (30 is connected to the top of the waterjet (3c).

8. A safe disposal machine for peritoneal dialysis liquid waste according to claim 1, wherein the flushing and disinfection device (1) comprises spray pipes (40) provided on both sides of the inside of the box main body (1), and the spray pipes (40) are connected to the outside of the clear water pipe (41) and disinfection pipe (42); the box main body (1) is connected with a clear water tank (43) for placing clear water and a disinfection tank (44) for placing disinfection solution on the top, and the clear water pipe (41) and disinfection pipe (42) are connected with the clear water tank (43) and the disinfection tank (44) respectively.

\* \* \* \* \*